United States Patent [19]

Suga

[11] 3,930,397

[45] Jan. 6, 1976

[54] COMBUSTION TESTING APPARATUS

[76] Inventor: Shigeru Suga, Yoyogi 5-20-2, Shibuya-ku, Tokyo, Japan

[22] Filed: Aug. 28, 1974

[21] Appl. No.: 501,454

[52] U.S. Cl. .................................. 73/15 R; 73/15
[51] Int. Cl.² ........................................ G01N 25/00
[58] Field of Search ..................... 73/15, 159, 160

[56] References Cited
UNITED STATES PATENTS

| | | | |
|---|---|---|---|
| 2,636,388 | 4/1953 | Biegen .................................. | 73/15 |
| 3,148,531 | 9/1964 | Stoll et al. ............................. | 73/15 |
| 3,665,750 | 5/1972 | Dawn et al. ........................... | 73/15 |

*Primary Examiner*—Herbert Goldstein
*Attorney, Agent, or Firm*—Wenderoth, Lind & Ponack

[57] ABSTRACT

An automatic combustion tester is disclosed. A burner is provided and is movable by a moving means between a first position adjacent a rigidly supported test piece and a second position. The burner is connected by a first conduit to a lateral tube which is, in turn, connected to a gas bomb by a coupling means. A flame timer is used for controlling the time during which a test piece is exposed to flames from the burner during a cycle. A down-time timer is provided for controlling the time during which the flame is removed from the test piece during a cycle. A heat shield is provided along with means for moving the heat shield between a position intermediate the test piece and the adjacent bunsen burner and a position removed therefrom. First and second microswitches are positioned to contact the conduit when the burner reaches its first and second positions. The first switch controls the heat shield and the second switch is coupled to a counter means for deactivating the system after a predetermined number of cycles of operation.

3 Claims, 3 Drawing Figures

REPEAT NUMBERS

REPEAT NUMBERS

COMBUSTION TESTING APPARATUS

BACKGROUND OF THE INVENTION

1. Field of the Invention

This invention relates to testers for determining combustibility of materials. More particularly, this invention relates to devices using an injection needle, etc., to periodically blow a fine flame onto a test piece for a definite period of time, with a predetermined non-exposure period between flame exposure periods. The operation is repeated to determine the number of cycles required until the test piece begins to burn, to determine whether the test piece catches fire after being subjected to the flame for a predetermined number of cycles, or to inspect combustibility by dividing the time of residual combustion after a number, e.g., five of successive cycles of, e.g., three seconds of flame exposure and, e.g., three seconds down time by the volume lost during the operation.

2. Description of the Prior Art

Various flame tests, particularly the last above-noted test, are conducted by hand. In this case, however, human error is unavoidable and results in very poor precision. For example, if the flame was successively applied five times for three seconds each time, i.e., a total of 15 seconds, the error accumulated through human inaccuracy may result in actual flame contact time of as little as 13 seconds or as long as 18 seconds.

The flame exposure period commences after the flame of the burner is brought into contact with the test piece. However, certain materials are easily affected or melted by the flame before it is actually brought to the predetermined position and wide variations in test results are obtained when testing these materials.

SUMMARY OF THE INVENTION

It is an object of the instant invention to provide a new and improved combustion testing system which minimizes error and is automated.

It is a further object of the subject invention to provide an improved combustion testing system that will produce accurate results even when easily combustible material is being tested.

DETAILED DESCRIPTION OF THE PREFERRED EMBODIMENTS

Figure 1:
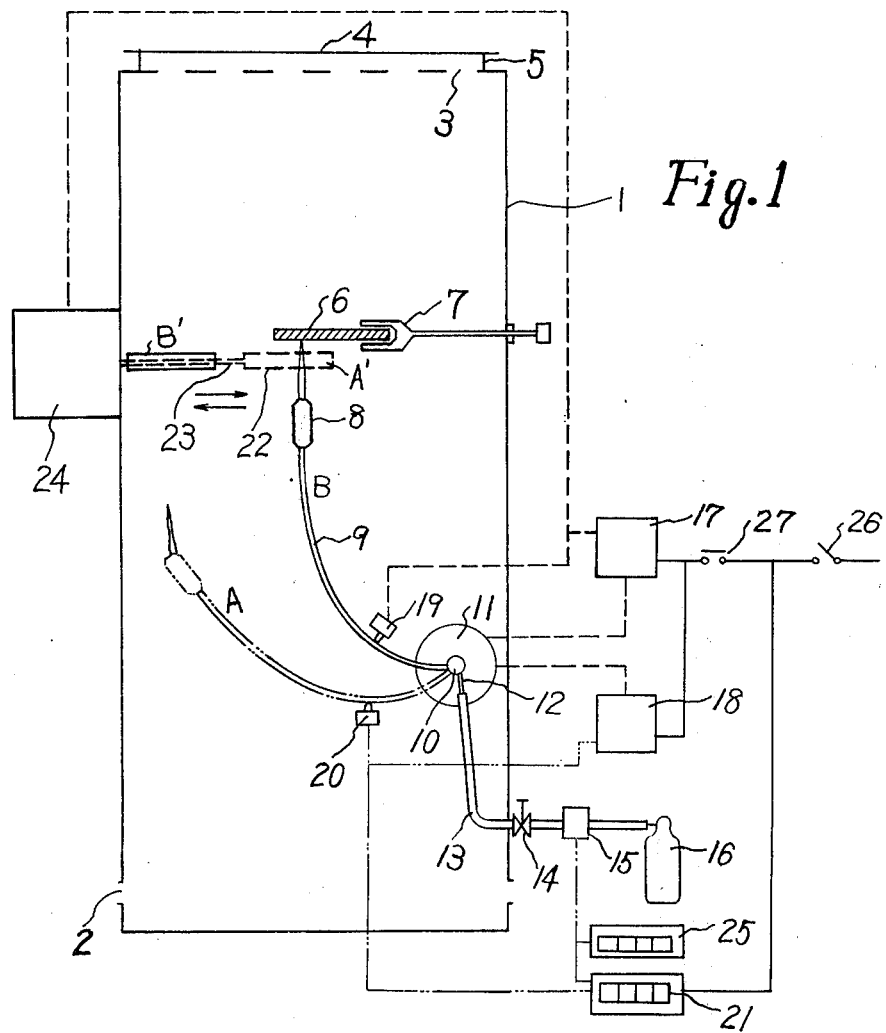
FIG. 1 is a schematic view of a preferred embodiment of the instant invention.

A test chamber 1 is made of a corrosion-resistant metal and has an air-inlet port 2 at the lower end and exhaust port 3 and top plate 4 at the upper portion thereof. The chamber communicates with the external atmosphere through clearance 5 between the top plate and the exhaust port. A test piece 6 is held by a test-piece support 7 at the center of the test chamber.

Burner 8 is positioned immediately below the test piece and supplied with a combustible gas (such as butane) through conduit 9. One end of the conduit 9 is connected to lateral tube 10 which is, in turn, directly connected to a burner moving means 11. The burner moves between positions A and B by means of the moving means 11 for selectively exposing the test piece to the flame. The lateral tube 10 is equipped with a hose port 12 and is thereby connected to a gas bomb 16 through rubber tube 13, needle valve 14 and electromagnetic valve 15.

The burner moving means 11 is electrically driven by a flame timer 17 which controls the flame time and by a down-time timer 18 which controls the time during each cycle when the test piece is not exposed to the burner flame. Successive switching between the flame timer and the down-time timer is dependent upon two microswitches, 19 and 20, that are actuated by the position of the burner. As shown, microswitch 20 is coupled to down-time timer 18 while microswitch 19 is coupled to flame timer 17 for respective control thereof. A counter 21 is connected to the microswitch 20 and receives an input every time the burner actuates microswitch 20. Hence by appropriately setting a desired number of cycles on the counter, operation of the electromagnetic valve and the timer 18 can be stopped automatically when the set number is reached. At the same time that this operation ceases, a residual-flame timer 25 is activated by counter 21 to begin measuring time.

The testing is started by activating switch 26, igniting the burner, adjusting the flame length, and depressing start switch 27.

Between the test piece and the burner a heat-shielding plate 22 is provided. This plate is moved reciprocally along the drive axis 23 by plate moving means 24 in order to selectively expose the test piece to the flame and to shield the test piece therefrom. When the burner is at the position A, the heat-shielding plate is at the position A′ to shield the test piece from the flame. When the burner reaches a position adjacent the test piece (position B), the heat-shielding plate moves to the position B′ and flame touches the test piece for the first time.

This eliminates the prior art problems relating to the inability to precisely control exposure time of the sample. Moreover, this overcomes the prior art difficulties encountered in the testing of readily combustible materials.

Figure 2:
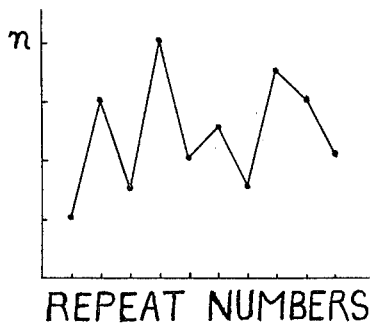
FIG. 2 depicts data values obtained by means of prior art combustion testing systems.
Figure 3:
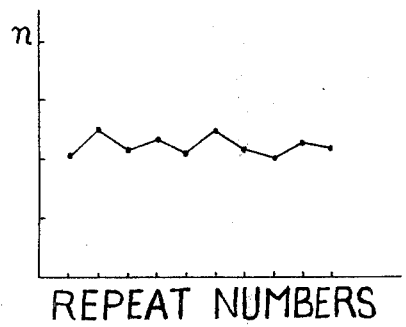
FIG. 3 shows data values obtained by using the improved combustion testing apparatus of the subject disclosure.

FIG. 2 depicts the experimental results obtained by using the prior art manual method. The parameter computed was the residual time of combustion (t), as determined by observing elapsed time on residual-flame timer 25 when residual burning is observed to be completed, of a test piece after 5 cycles of 3 second flame exposure, divided by the volume (v) of the test piece lost during burning, and is represented in terms of the value of combustibility $n = t/v$. Ten tests were performed and the values were dispersed as shown in FIG. 2. It should be apparent that the test results were widely scattered. In contrast, when similar tests were performed utilizing the device of the subject invention, very uniform results were obtained, as shown in FIG. 3.

It is to be understood that there are many variations of the above-detailed preferred embodiment and they are to be considered within the scope of the appended claims unless departing from the spirit of the invention.

I claim:

1. A device for testing combustion properties of a testpiece, said device comprising:
   a test chamber having an air inlet port and an exhaust port therein;

a test piece support positioned to support a test piece within said test chamber;

a burner means movable between a first position adjacent said test piece within said test chamber and a second position remote from said test piece within said test chamber;

a lateral tube coupled to said burner means;

a gas bomb;

means coupling said lateral tube to said gas bomb for selectively supplying gas to said lateral tube;

a flame timer for controlling the time during which a test piece is exposed to flame from the burner means during a cycle;

a down-time timer for controlling the time during which the flame is removed from the test piece during a cycle;

a burner moving means operatively controlled by said flame timer and said down-time timer and coupled to said lateral tube for moving said lateral tube and said burner means between said first and second positions at predetermined intervals determined by the time settings of said flame timer and said down-time timer;

a first microswitch positioned to contact said burner means when said burner means is in said first position;

a second microswitch positioned to contact said burner means when said burner means is in said second position;

a counter means coupled to said coupling means and said second microswitch for halting gas flow upon detection of predetermined number of contacts between said second microswitch and said burner means;

a residual flame timer coupled to and operable by said counter means for providing an indication of time lapse beginning with said halting of said gas flow;

a heat shield; and means operatively positioned for moving said heat shield between a position intermediate said test piece and said first position of said burner means and a position remote therefrom, said moving means being coupled to said heat shield and to said first microswitch, whereby said test piece is shielded from flame until said burner means is adjacent thereto, said test piece being subjected to a predetermined number of periodic exposures to flame, the length of the periodic exposures and the hiatus therebetween being precisely controlled.

2. A device as claimed in claim 1, wherein said burner means comprises a burner head and a first conduit connected at a first end thereof to said burner head and at a second end thereof to said lateral tube.

3. A device as claimed in claim 2, wherein said coupling means comprises a second conduit coupled to said lateral conduit by a hose port, and a needle valve and an electro magnetic valve operatively disposed along said second conduit.

* * * * *